United States Patent
Anderson et al.

(10) Patent No.: US 8,133,553 B2
(45) Date of Patent: Mar. 13, 2012

(54) PROCESS FOR FORMING A CERAMIC LAYER

(75) Inventors: Jeffrey P. Anderson, Warsaw, IN (US); Oludele Popoola, Granger, IN (US)

(73) Assignee: Zimmer, Inc., Warsaw, IN (US)

( * ) Notice: Subject to any disclaimer, the term of this patent is extended or adjusted under 35 U.S.C. 154(b) by 1013 days.

(21) Appl. No.: 11/764,585

(22) Filed: Jun. 18, 2007

(65) Prior Publication Data

US 2008/0312748 A1 Dec. 18, 2008

(51) Int. Cl.
*C23C 14/04* (2006.01)
*C23C 14/06* (2006.01)
*A61F 2/36* (2006.01)

(52) U.S. Cl. ..... 427/531; 427/2.24; 427/2.26; 427/2.27; 427/523; 427/529; 427/585; 623/23.11

(58) Field of Classification Search .......... None
See application file for complete search history.

(56) References Cited

U.S. PATENT DOCUMENTS

| | | |
|---|---|---|
| 2,987,352 A | 6/1961 | Watson |
| 3,605,123 A | 9/1971 | Hahn |
| 3,643,658 A | 2/1972 | Steinemenan |
| 3,677,795 A | 7/1972 | Bokros et al. |
| 4,004,064 A | 1/1977 | Kessler |
| 4,145,764 A | 3/1979 | Suzuki et al. |
| 4,487,808 A | 12/1984 | Lambert |
| 4,563,489 A | 1/1986 | Urist |
| 4,570,271 A | 2/1986 | Sump |
| 4,671,824 A | 6/1987 | Haygarth |
| 4,713,076 A | 12/1987 | Draenert |
| 4,923,471 A | 5/1990 | Morgan |
| 5,037,438 A | 8/1991 | Davidson |
| 5,084,050 A | 1/1992 | Draenert |
| 5,178,201 A | 1/1993 | Ahlers |
| 5,198,308 A | 3/1993 | Shetty |
| 5,258,022 A | 11/1993 | Davidson |
| 5,282,861 A | 2/1994 | Kaplan |

(Continued)

FOREIGN PATENT DOCUMENTS

CH 657519 9/1986

(Continued)

OTHER PUBLICATIONS

C. Piconi, Zirconia as a ceramic biomaterial, Biomaterials 20 (1999) 1-25.

(Continued)

*Primary Examiner* — Timothy Meeks
*Assistant Examiner* — Joseph Miller, Jr.
(74) *Attorney, Agent, or Firm* — Cook Alex Ltd.

(57) ABSTRACT

A process for forming a ceramic layer comprising a compound of a metal on a deposition surface of a workpiece comprises providing a reactive gas, selecting the amounts of a vapor of the metal and ions of the metal relative to each other, generating the metal vapor, and projecting an ion beam of the metal ions. The metal vapor, the metal ions, and the reactive gas form the ceramic layer with a desired structure. The process may include the step of controlling a deposition surface temperature. In one embodiment, the metal vapor comprises zirconium vapor and the ion beam comprises zirconium ions. The relative amounts of the zirconium vapor and the zirconium ions are selected to form a zirconia ceramic layer on the deposition surface. The zirconia may have multiple crystal phases that are formed according to a predetermined ratio.

11 Claims, 4 Drawing Sheets

U.S. PATENT DOCUMENTS

| | | | |
|---|---|---|---|
| 5,302,414 A | 4/1994 | Alkhimov | |
| 5,316,594 A | 5/1994 | Kemp | |
| 5,323,954 A | 6/1994 | Shetty | |
| 5,324,009 A | 6/1994 | Kemp | |
| 5,383,934 A | 1/1995 | Armini | |
| 5,397,796 A | 3/1995 | Zoller | |
| 5,399,207 A | 3/1995 | Kemp | |
| 5,409,703 A | 4/1995 | McAnalley et al. | |
| 5,447,724 A | 9/1995 | Helmus | |
| 5,458,653 A | 10/1995 | Davidson | |
| 5,464,440 A | 11/1995 | Johansson | |
| 5,470,829 A | 11/1995 | Prisell | |
| 5,492,697 A | 2/1996 | Boyan | |
| 5,509,899 A | 4/1996 | Fan et al. | |
| 5,529,914 A | 6/1996 | Hubbell | |
| 5,534,524 A | 7/1996 | Bonewald | |
| 5,535,810 A | 7/1996 | Compton | |
| 5,543,441 A | 8/1996 | Rhee | |
| 5,550,178 A | 8/1996 | Desai | |
| 5,554,594 A | 9/1996 | Zoller | |
| 5,565,407 A | 10/1996 | Southard | |
| 5,569,463 A | 10/1996 | Helmus | |
| 5,573,934 A | 11/1996 | Hubbell | |
| 5,612,052 A | 3/1997 | Shalaby | |
| 5,631,011 A | 5/1997 | Wadstrom | |
| 5,658,334 A | 8/1997 | Caldarise | |
| 5,658,935 A | 8/1997 | Kingler | |
| 5,665,118 A | 9/1997 | LaSalle | |
| 5,688,855 A | 11/1997 | Stoy | |
| 5,713,410 A | 2/1998 | LaSalle | |
| 5,714,159 A | 2/1998 | Shalaby | |
| 5,736,160 A | 4/1998 | Ringeisen | |
| 5,788,979 A | 8/1998 | Alt | |
| 5,801,033 A | 9/1998 | Hubbell | |
| 5,824,651 A | 10/1998 | Nanci | |
| 5,834,274 A | 11/1998 | Hubbell | |
| 5,843,743 A | 12/1998 | Hubbell | |
| 5,866,113 A | 2/1999 | Hendriks | |
| 5,893,846 A | 4/1999 | Bales | |
| 5,925,552 A | 7/1999 | Keogh | |
| 5,928,916 A | 7/1999 | Keogh | |
| 5,932,299 A | 8/1999 | Katoot | |
| 5,947,893 A | 9/1999 | Agrawal | |
| 5,980,974 A | 11/1999 | Armini et al. | |
| 6,004,943 A | 12/1999 | Shi | |
| 6,080,488 A | 6/2000 | Hostettler et al. | |
| 6,099,562 A | 8/2000 | Ding | |
| 6,110,483 A | 8/2000 | Whitbourne et al. | |
| 6,120,536 A | 9/2000 | Ding | |
| 6,121,027 A | 9/2000 | Clapper | |
| 6,153,252 A | 11/2000 | Hossainy | |
| 6,166,173 A | 12/2000 | Mao | |
| 6,176,849 B1 | 1/2001 | Yang et al. | |
| 6,177,095 B1 | 1/2001 | Swahney | |
| 6,179,817 B1 | 1/2001 | Zhong | |
| 6,197,051 B1 | 3/2001 | Zhong | |
| 6,238,687 B1 | 5/2001 | Mao | |
| 6,254,634 B1 | 7/2001 | Anderson | |
| 6,258,121 B1 | 7/2001 | Yang | |
| 6,284,305 B1 | 9/2001 | Ding | |
| 6,309,660 B1 | 10/2001 | Hsu | |
| 6,313,119 B1 | 11/2001 | Peyman | |
| 6,316,522 B1 | 11/2001 | Loomis | |
| 6,322,797 B1 | 11/2001 | Mao | |
| 6,368,658 B1 | 4/2002 | Schwarz | |
| 6,395,023 B1 | 5/2002 | Summers | |
| 6,395,029 B1 | 5/2002 | Levy | |
| 6,410,044 B1 | 6/2002 | Chudzik et al. | |
| 6,413,539 B1 | 7/2002 | Shalaby | |
| 6,451,373 B1 | 9/2002 | Hossainy | |
| 6,455,541 B1 | 9/2002 | Bonewald | |
| 6,461,631 B1 | 10/2002 | Dunn | |
| 6,486,232 B1 | 11/2002 | Wise | |
| 6,492,356 B1 | 12/2002 | Peyman | |
| 6,500,481 B1 | 12/2002 | Vanderlaan | |
| 6,506,437 B1 | 1/2003 | Harish | |
| 6,514,515 B1 | 2/2003 | Williams | |
| 6,514,734 B1 | 2/2003 | Clapper | |
| 6,528,080 B2 | 3/2003 | Dunn | |
| 6,540,746 B1 | 4/2003 | Buehler | |
| 6,544,472 B1 | 4/2003 | Compton | |
| 6,545,097 B2 | 4/2003 | Pinchuk | |
| 6,558,734 B2 | 5/2003 | Koulik | |
| 6,596,402 B2 | 7/2003 | Soerens | |
| 6,600,010 B2 | 7/2003 | Mao | |
| 6,613,088 B1 * | 9/2003 | Babizhayev | 623/6.62 |
| 6,620,194 B2 | 9/2003 | Ding | |
| 6,632,446 B1 | 10/2003 | Hubbell | |
| 6,656,517 B2 | 12/2003 | Michal | |
| 6,669,980 B2 | 12/2003 | Hansen | |
| 6,673,385 B1 | 1/2004 | Ding | |
| 6,692,790 B2 | 2/2004 | Liu | |
| 6,723,350 B2 | 4/2004 | Burrell | |
| 6,726,725 B2 | 4/2004 | Hunter et al. | |
| 6,730,324 B2 | 5/2004 | Troczynski | |
| 6,733,768 B2 | 5/2004 | Hossainy | |
| 6,743,521 B2 | 6/2004 | Hubbell | |
| 6,746,685 B2 | 6/2004 | Williams | |
| 6,749,639 B2 | 6/2004 | Lewallen | |
| 6,833,192 B1 | 12/2004 | Caruso | |
| 6,833,363 B2 | 12/2004 | Renier | |
| 6,855,329 B1 | 2/2005 | Shakesheff | |
| 6,866,860 B2 | 3/2005 | Nathan | |
| 6,869,445 B1 | 3/2005 | Johnson | |
| 6,872,799 B2 | 3/2005 | Nathan | |
| 6,881,766 B2 | 4/2005 | Hain | |
| 6,899,107 B2 | 5/2005 | Lewandrowski | |
| 6,899,731 B2 | 5/2005 | Li | |
| 6,921,811 B2 | 7/2005 | Zamora | |
| 6,923,986 B2 | 8/2005 | Pathak | |
| 6,923,996 B2 | 8/2005 | Epstein | |
| 6,945,448 B2 | 9/2005 | Medlin | |
| 6,946,443 B2 | 9/2005 | Blanchat | |
| 6,967,234 B2 | 11/2005 | Nathan | |
| 6,969,400 B2 | 11/2005 | Rhee | |
| 6,974,625 B2 | 12/2005 | Hunter et al. | |
| 6,986,899 B2 | 1/2006 | Hossainy | |
| 6,991,681 B2 | 1/2006 | Yoe | |
| 6,991,802 B1 | 1/2006 | Ahola | |
| 6,994,883 B2 | 2/2006 | Layrolle | |
| 6,998,134 B2 | 2/2006 | Schmidmaier | |
| 7,001,421 B2 | 2/2006 | Cheng | |
| 7,008,979 B2 | 3/2006 | Schottman | |
| 7,112,361 B2 | 9/2006 | Lynn | |
| 7,148,209 B2 | 12/2006 | Hoemann | |
| 7,157,096 B2 | 1/2007 | Zhang | |
| 7,163,715 B1 | 1/2007 | Kramer | |
| 7,185,695 B1 | 3/2007 | Santeler | |
| 7,186,811 B2 | 3/2007 | Lindholm | |
| 7,838,083 B1 * | 11/2010 | Youchison et al. | 427/529 |
| 2002/0018798 A1 | 2/2002 | Sewing | |
| 2002/0041899 A1 | 4/2002 | Chudzik | |
| 2002/0082552 A1 | 6/2002 | Ding | |
| 2002/0084194 A1 | 7/2002 | Redepenning | |
| 2002/0087184 A1 | 7/2002 | Eder | |
| 2002/0103526 A1 | 8/2002 | Steinke | |
| 2002/0111590 A1 | 8/2002 | Davila | |
| 2002/0119179 A1 | 8/2002 | Rezania | |
| 2002/0120333 A1 | 8/2002 | Keogh | |
| 2002/0131989 A1 | 9/2002 | Brown | |
| 2002/0151617 A1 | 10/2002 | Mao | |
| 2002/0165608 A1 | 11/2002 | Llanos | |
| 2002/0192182 A1 | 12/2002 | Massia | |
| 2003/0004568 A1 | 1/2003 | Ken | |
| 2003/0007991 A1 | 1/2003 | Masters | |
| 2003/0036794 A1 | 2/2003 | Ragheb et al. | |
| 2003/0083740 A1 | 5/2003 | Pathak | |
| 2003/0088307 A1 | 5/2003 | Shulze | |
| 2003/0099762 A1 | 5/2003 | Zhang | |
| 2003/0113478 A1 | 6/2003 | Dang | |
| 2003/0114937 A1 | 6/2003 | Leatherbury | |
| 2003/0117579 A1 | 6/2003 | Morris | |
| 2003/0118692 A1 | 6/2003 | Wang | |
| 2003/0124172 A1 | 7/2003 | Lopez | |
| 2003/0124368 A1 | 7/2003 | Lynn | |
| 2003/0129130 A1 | 7/2003 | Guire | |
| 2003/0157030 A1 | 8/2003 | Davis | |

| Pub. No. | Date | Name | | Pub. No. | Date | Name | |
|---|---|---|---|---|---|---|---|
| 2003/0185752 A1 | 10/2003 | Nathan | | 2005/0220843 A1 | 10/2005 | DeWitt | |
| 2003/0219562 A1 | 11/2003 | Rypacek | | 2005/0244363 A1 | 11/2005 | Hossainy | |
| 2003/0228364 A1 | 12/2003 | Nathan | | 2005/0244453 A1 | 11/2005 | Stucke | |
| 2003/0229393 A1 | 12/2003 | Kutryk | | 2005/0244459 A1 | 11/2005 | DeWitt | |
| 2004/0033249 A1 | 2/2004 | Sewing | | 2005/0245637 A1 | 11/2005 | Hossainy | |
| 2004/0039441 A1 | 2/2004 | Rowland | | 2005/0251250 A1 | 11/2005 | Verhoeven | |
| 2004/0044404 A1 | 3/2004 | Stucke | | 2005/0255142 A1 | 11/2005 | Chudzik | |
| 2004/0049265 A1 | 3/2004 | Ding | | 2005/0266038 A1 | 12/2005 | Glauser | |
| 2004/0051201 A1 | 3/2004 | Greenhalgh | | 2005/0266077 A1 | 12/2005 | Royer | |
| 2004/0063654 A1 | 4/2004 | Davis | | 2005/0271700 A1 | 12/2005 | DesNoyer | |
| 2004/0081745 A1 | 4/2004 | Hansen | | 2005/0271701 A1 | 12/2005 | Cottone | |
| 2004/0086493 A1 | 5/2004 | Hubbell | | 2005/0274478 A1 | 12/2005 | Verner | |
| 2004/0086543 A1 | 5/2004 | Keogh | | 2005/0283224 A1 | 12/2005 | King | |
| 2004/0091462 A1 | 5/2004 | Lin | | 2005/0288229 A1 | 12/2005 | Sindrey | |
| 2004/0091603 A1 | 5/2004 | Priewe | | 2006/0003008 A1 | 1/2006 | Gibson | |
| 2004/0093080 A1 | 5/2004 | Helmus | | 2006/0008500 A1 | 1/2006 | Chavan | |
| 2004/0106985 A1 | 6/2004 | Jang | | 2006/0009839 A1 | 1/2006 | Tan | |
| 2004/0109892 A1 | 6/2004 | Shalaby | | 2006/0013850 A1 | 1/2006 | Domb | |
| 2004/0117007 A1 | 6/2004 | Whitbourne | | 2006/0018948 A1 | 1/2006 | Guire | |
| 2004/0120982 A1 | 6/2004 | Diana | | 2006/0025848 A1 | 2/2006 | Weber | |
| 2004/0126405 A1 | 7/2004 | Sahatjian | | 2006/0035854 A1 | 2/2006 | Goldstein | |
| 2004/0133271 A1 | 7/2004 | Jang | | 2006/0036311 A1 | 2/2006 | Nakayama | |
| 2004/0137066 A1 | 7/2004 | Jayaraman | | 2006/0036316 A1 | 2/2006 | Zeltinger | |
| 2004/0138695 A1 | 7/2004 | Li | | 2006/0039947 A1 | 2/2006 | Schmidmaier | |
| 2004/0147999 A1 | 7/2004 | Udipi | | 2006/0039950 A1 | 2/2006 | Zhou | |
| 2004/0157073 A1 | 8/2004 | Burrell | | 2006/0045901 A1 | 3/2006 | Weber | |
| 2004/0170752 A1 | 9/2004 | Luthra | | 2006/0051978 A1* | 3/2006 | Li et al. | 438/785 |
| 2004/0172121 A1 | 9/2004 | Eidenschink | | 2006/0057277 A1 | 3/2006 | Chappa | |
| 2004/0185086 A1 | 9/2004 | Massia | | 2006/0067969 A1 | 3/2006 | Lu | |
| 2004/0215313 A1 | 10/2004 | Cheng | | 2006/0093646 A1 | 5/2006 | Cima | |
| 2004/0215336 A1 | 10/2004 | Udipi | | 2006/0105018 A1 | 5/2006 | Epstein | |
| 2004/0241202 A1 | 12/2004 | Chluba | | 2006/0121081 A1 | 6/2006 | Labrecque | |
| 2004/0241234 A1 | 12/2004 | Vilkov | | 2006/0135652 A1* | 6/2006 | Kasseh et al. | 523/205 |
| 2005/0015442 A1 | 1/2005 | Eidenschink | | 2006/0165754 A1 | 7/2006 | Ranade | |
| 2005/0025752 A1 | 2/2005 | Kutryk | | 2006/0188541 A1 | 8/2006 | Richelsoph | |
| 2005/0025799 A1 | 2/2005 | Hossainy | | 2006/0198868 A1 | 9/2006 | DeWitt | |
| 2005/0031689 A1 | 2/2005 | Shults | | 2006/0204536 A1 | 9/2006 | Shults | |
| 2005/0031793 A1 | 2/2005 | Moeller | | 2006/0204542 A1 | 9/2006 | Zhang | |
| 2005/0036946 A1 | 2/2005 | Pathak | | 2006/0210598 A1 | 9/2006 | Evans | |
| 2005/0048121 A1 | 3/2005 | East | | 2006/0210602 A1 | 9/2006 | Sehl | |
| 2005/0049694 A1 | 3/2005 | Neary | | 2006/0216772 A1 | 9/2006 | Grinstaff | |
| 2005/0060028 A1 | 3/2005 | Horres | | 2006/0222681 A1 | 10/2006 | Richard | |
| 2005/0079200 A1 | 4/2005 | Rathenow | | 2006/0222756 A1 | 10/2006 | Davila | |
| 2005/0084515 A1 | 4/2005 | Udipi | | 2006/0233801 A1 | 10/2006 | Brunkow | |
| 2005/0085605 A1 | 4/2005 | Nathan | | 2006/0233841 A1 | 10/2006 | Brodbeck | |
| 2005/0095267 A1 | 5/2005 | Campbell | | 2006/0233941 A1 | 10/2006 | Olson | |
| 2005/0101692 A1 | 5/2005 | Sohier | | 2006/0233944 A1* | 10/2006 | Popoola et al. | 427/2.24 |
| 2005/0106204 A1 | 5/2005 | Hossainy | | 2006/0240063 A9 | 10/2006 | Hunter | |
| 2005/0112170 A1 | 5/2005 | Hossainy | | 2006/0246103 A1 | 11/2006 | Ralph | |
| 2005/0112172 A1 | 5/2005 | Pacetti | | 2006/0246105 A1 | 11/2006 | Molz | |
| 2005/0129731 A1 | 6/2005 | Horres | | 2006/0246110 A1 | 11/2006 | Brandon | |
| 2005/0142393 A1* | 6/2005 | Boutwell et al. | 428/701 | 2006/0247793 A1 | 11/2006 | Trieu | |
| 2005/0147647 A1 | 7/2005 | Glauser | | 2006/0251824 A1 | 11/2006 | Boulais | |
| 2005/0149171 A1 | 7/2005 | McCullagh | | 2006/0252981 A1 | 11/2006 | Matsuda | |
| 2005/0152955 A1 | 7/2005 | Akhave | | 2006/0257377 A1 | 11/2006 | Atala | |
| 2005/0153429 A1 | 7/2005 | Liebmann-Vinson | | 2006/0263830 A1 | 11/2006 | Grinstaff | |
| 2005/0154450 A1 | 7/2005 | Larson | | 2006/0263831 A1 | 11/2006 | Grinstaff | |
| 2005/0158359 A1 | 7/2005 | Epstein | | 2006/0264531 A1 | 11/2006 | Zhao | |
| 2005/0159746 A1* | 7/2005 | Grob et al. | 606/61 | 2006/0286064 A1 | 12/2006 | Turnell | |
| 2005/0165128 A1 | 7/2005 | Cohn | | 2006/0286071 A1 | 12/2006 | Epstein | |
| 2005/0169882 A1 | 8/2005 | Lowe | | 2006/0293406 A1 | 12/2006 | Bennett | |
| 2005/0169969 A1 | 8/2005 | Li | | 2007/0016163 A1 | 1/2007 | Santini | |
| 2005/0180919 A1 | 8/2005 | Tedeschi | | 2007/0020308 A1 | 1/2007 | Richard | |
| 2005/0183259 A1 | 8/2005 | Eidenschink | | 2007/0020469 A1 | 1/2007 | Wood | |
| 2005/0187376 A1 | 8/2005 | Pacetti | | 2007/0026043 A1 | 2/2007 | Guan | |
| 2005/0187602 A1 | 8/2005 | Eidenschink | | 2007/0032882 A1 | 2/2007 | Lodhi | |
| 2005/0187611 A1 | 8/2005 | Ding | | 2007/0037737 A1 | 2/2007 | Hoemmann | |
| 2005/0191333 A1 | 9/2005 | Hsu | | 2007/0038300 A1 | 2/2007 | Bao | |
| 2005/0208093 A1 | 9/2005 | Glauser | | 2007/0041952 A1 | 2/2007 | Guilak | |
| 2005/0208100 A1 | 9/2005 | Weber | | 2007/0042017 A1 | 2/2007 | Kutryk | |
| 2005/0208200 A1 | 9/2005 | Ding | | 2007/0043374 A1 | 2/2007 | Evans | |
| 2005/0214339 A1 | 9/2005 | Tang | | 2007/0043433 A1 | 2/2007 | Chandrasekaran | |
| 2005/0214916 A1* | 9/2005 | Absar et al. | 435/168 | 2007/0045902 A1 | 3/2007 | Brauker | |
| 2005/0215722 A1 | 9/2005 | Pinchunk | | 2007/0048291 A1 | 3/2007 | Mang | |
| 2005/0220837 A1 | 10/2005 | Disegi | | 2007/0048292 A1 | 3/2007 | Morita | |
| 2005/0220839 A1 | 10/2005 | DeWitt | | 2007/0053963 A1 | 3/2007 | Hotchkiss | |
| 2005/0220840 A1 | 10/2005 | DeWitt | | 2007/0054127 A1 | 3/2007 | Hergenrother | |
| 2005/0220841 A1 | 10/2005 | DeWitt | | 2007/0055095 A1 | 3/2007 | Chu | |
| 2005/0220842 A1 | 10/2005 | DeWitt | | 2007/0055367 A1 | 3/2007 | Kutryk | |

FOREIGN PATENT DOCUMENTS

| | | |
|---|---|---|
| EP | 0372662 | 6/1990 |
| EP | 0616814 | 3/1994 |
| EP | 1055743 * | 11/2000 |
| EP | 1273303 | 1/2003 |
| EP | 1144018 | 3/2004 |
| EP | 1806155 | 7/2007 |
| WO | WO9307835 | 4/1993 |
| WO | WO9628117 | 9/1996 |
| WO | WO9738469 | 10/1997 |
| WO | WO0139680 | 6/2001 |
| WO | WO0182989 | 11/2001 |
| WO | WO 03/077772 A1 | 9/2003 |
| WO | WO2005120203 | 12/2005 |
| WO | WO2007014279 | 2/2007 |
| WO | WO2007038559 | 4/2007 |
| WO | WO2007053022 | 5/2007 |

OTHER PUBLICATIONS

ISR/WO From PCT/US2009/032608, 2009.
Jegnathian Karthiekeyan. Cold Spray Technology, Mar. 2005, pp. 33-35, ASB Industries, Barberton, OH.
ISR/WO From PCT/US2009/031502, 2009.
ISR from Application No. 08252074.2, 2008.
Uthoff. J. Orthop. Scie., 11:118-126 (2006).
Aleksyniene. Medicinia (Kaunus), vol. 40 (9): 842-849 (2004).
Termaat. J. Bone and Joint Surg., 870A(6): 1366-1378 (2005).
Morris. J. Bone and Joint Surg., 87-A(7), 1608-1618 (2005).
Pavoor. Biomat., 27, 1527-1533 (2006).

\* cited by examiner

PROCESS FOR FORMING A CERAMIC LAYER

FIELD OF THE INVENTION

This invention relates to processes for forming ceramic layers, and, more particularly, to a process for forming a ceramic layer having a desired structure with a predetermined ratio of crystal phases.

BACKGROUND OF THE INVENTION

Ion beam assisted deposition (IBAD) is a process used to deposit thin, adherent coatings onto a surface of a substrate. In this process, the substrate is placed into a vacuum chamber and a vapor and an ion beam are simultaneously used to deposit the thin coating onto the substrate. Ion beam assisted deposition has been used to deposit many different materials, including, for example, zirconium dioxide.

Zirconium dioxide or zirconia has found application on orthopedic implants. Zirconia exhibits many of the preferred and desired attributes for use in vivo. For example, zirconia is biologically inert, hard, and can be formed as a smooth film on an articular surface of an orthopedic implant. Unfortunately, the use of zirconia is not without difficulty.

One difficulty is that zirconia, like many other oxide and nonoxide ceramics, has multiple phases. Zirconia has a monoclinic phase, a tetragonal phase, and a cubic phase. In particular, the difficulty with zirconia arises due to a volume expansion that a zirconia unit cell undergoes when it transforms from tetragonal to monoclinic. The volume expansion is approximately 4%. When zirconia transforms, the volume expansion results in an enormous stress increase within a product made of zirconia. In fact, the stresses that form in bulk components of pure zirconia will often cause spontaneous catastrophic failure of the component. In other applications, particularly in orthopedic implant applications, the phase transformation may result in surface roughening as isolated pockets of tetragonal zirconia transform into monoclinic zirconia, essentially causing the surface to buckle outward as it attempts to expand. Surface roughening on articular surfaces is unacceptable.

Therefore, what is needed in the art is a process for forming a ceramic layer where a particular crystal structure of the ceramic layer may be selected. In addition, what is needed in the art is a process that permits selection or adjustment of the relative amounts of the constituents according to a relationship between the constituents and the ceramic layer such that the ceramic layer is formed with a desired structure having a predetermined ratio of two or more crystal structures. Furthermore, what is needed is a process for forming a zirconia ceramic layer having a desired structure comprising two or more crystal phases, but that does not roughen due to tetragonal to monoclinic zirconia transformation.

SUMMARY OF THE INVENTION

The present invention provides a process for forming a ceramic layer comprising a compound of a metal on a deposition surface of a workpiece. An initial step of the process includes providing a reactive gas in fluid communication with the deposition surface. The process includes generating a vapor of the metal in fluid communication with the deposition surface. The process also includes projecting an ion beam comprising a plurality of ions of the metal on to the deposition surface. In addition, the process includes selecting an amount of the metal vapor relative to an amount of the metal ions. The process may include adjusting the ratio of the metal vapor to the metal ions. In summary, the deposition surface is in fluid communication with the reactive gas, the metal vapor, and the metal ions, which react at the selected amounts to form the ceramic layer with a desired structure on the deposition surface.

In another embodiment, the ceramic layer may comprise zirconia and the desired structure may be tetragonal, monoclinic, or cubic zirconia. In another embodiment of the invention, the desired structure may be formed in a predetermined ratio of at least two crystal phases by selecting the ratio of a zirconium vapor to a plurality of zirconium ions.

In another embodiment the workpiece is an orthopedic implant. The zirconia layer may be comprised of monoclinic, tetragonal, or cubic phases or a combination thereof formed on the orthopedic implant. In yet another embodiment, the zirconia layer may be formed in a predetermined ratio of the monoclinic phase to the tetragonal phase such that the monoclinic to tetragonal phase transformation is suppressed.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1A:
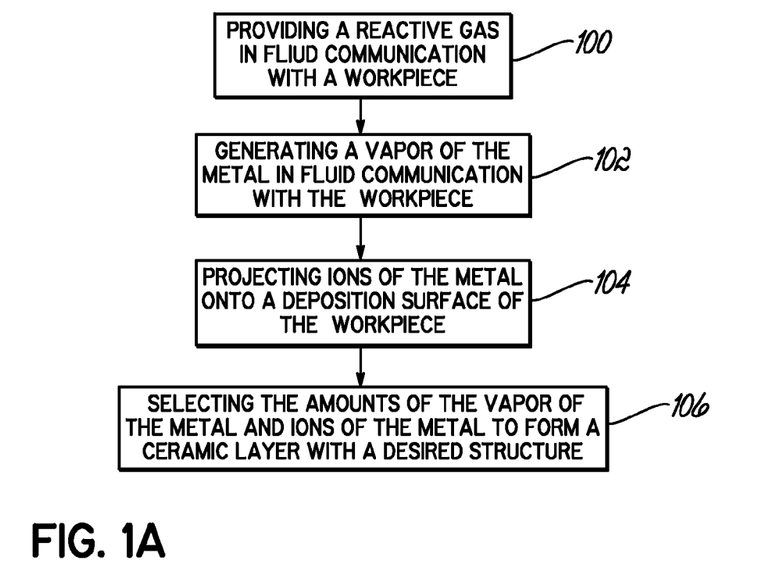
FIG. 1A is a process flow diagram of one embodiment of the process of the present invention.
Figure 1B:
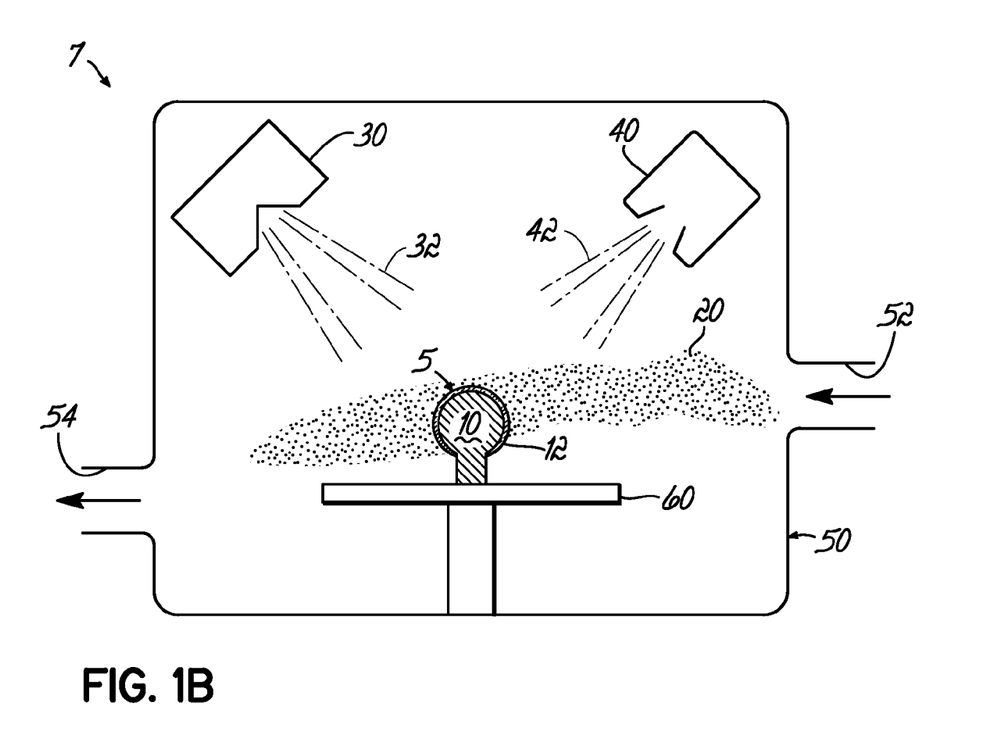
FIG. 1B is an illustration of one embodiment of the process showing formation of a ceramic layer on a workpiece.

One embodiment of a process for forming a ceramic layer 5 comprising a compound of a metal is illustrated by the process flow diagram of FIG. 1A and an apparatus 7 depicted in FIG. 1B. In an initial step of the process in 100, a workpiece 10 is positioned in a chamber 50 of the apparatus 7 and a reactive gas 20 is provided in fluid communication with a deposition surface 12 of the workpiece 10. The process further includes using an evaporator 30 to generate a vapor 32 of the metal and direct it to the workpiece 10, in 102, as depicted in FIG. 1B. The process further includes using an ion source 40 to form ions 42 of the metal. The metal ions 42 are projected, in 104, onto the deposition surface 12, generally in the form of an ion beam. The process further includes selecting the amount of the metal vapor 32 relative to the amount of the metal ions 42 in 106. The deposition surface 12 is thus exposed to the reactive gas 20, the metal vapor 32, and the metal ions 42, which react at selected amounts to form the ceramic layer 5 on the deposition surface 12. The process is not limited to the order as described herein. That is, the steps may be performed in other orders, including simultaneously.

In one embodiment, the process may also include adjusting the ratio of the metal vapor 32 to the metal ions 42 to deposit the ceramic layer 5 with another desired structure. Thus, in accordance with the inventive process, multiple desired structures may be interwoven or layered on the deposition surface 12 by adjusting the ratio of the metal vapor 32 to the metal ions 42 while forming the ceramic layer 5.

In another embodiment, the workpiece 10 and the reactive gas 20 are contained within the chamber 50 and the pressure, the flow rate, and the constituents of the reactive gas 20 are controlled through a supply port 52. The chamber 50 may also have a vacuum port 54 in fluid communication with a vacuum system (not shown) for reducing the pressure inside the chamber 50 prior to both generating the metal vapor 32 and forming the metal ions 42.

Selecting and adjusting the ratio of the metal vapor 32 to the metal ions 42, refers to choosing the ratio according to a relationship between the ratio of the metal vapor 32 to the metal ions 42 and the desired structure of the ceramic layers. The relationship being identified by prior variation of the ratio and quantification of the desired structure formed with each variation. For example, variations in the ratio of the metal vapor 32 to the metal ions 42 in conjunction with the reactive gas 20 are used to form a ceramic layer 5. The desired structure of the ceramic layer 5 for those variations is then quantified. The relationship between the ratio and the desired structure is thus established. Therefore, subsequent selection or adjustment of the ratio of the metal vapor 32 to the metal ions 42 forms the ceramic layer 5 having the desired structure. As the term is used herein, the desired structure is a crystal phase or phases deposited by the reaction of the metal vapor 32 and metal ions 42 and the reactive gas 20.

In one embodiment, the relationship between the ratio of the metal vapor 32 to the metal ions 42 is one that deposits a ceramic layer 5 having a desired structure containing at least two crystal phases. Furthermore, those crystal phases may be formed in a predetermined ratio. In other words, the amount of each crystal phase may be predicted. For example, the predetermined ratio may be represented by a volume of a first crystal phase to a volume of a second crystal phase. One skilled in the art will observe that adjusting or selecting another ratio of the metal vapor 32 to the metal ions 42 may produce a second ratio of the volumes of the first and second crystal phases. Therefore, the invention may permit layering multiple desired structures each having differing volumes of crystal phases. By way of example and not limitation, the crystal phases may comprise crystal phases for $SiO_2$, $ZrO_2$, $TiO_2$, $AS_2O_3$, $CaTiO_3$, $Al_2SiO_5$, BN, ZnS, $FeS_2$, or other ceramic systems with polymorphic characteristics. As one skilled in the art will observe, a reactive gas 20 comprising oxygen will form oxides, while a reactive gas comprising sulfur or nitrogen will form sulfide compounds and nitride compounds, respectively.

Figure 6:
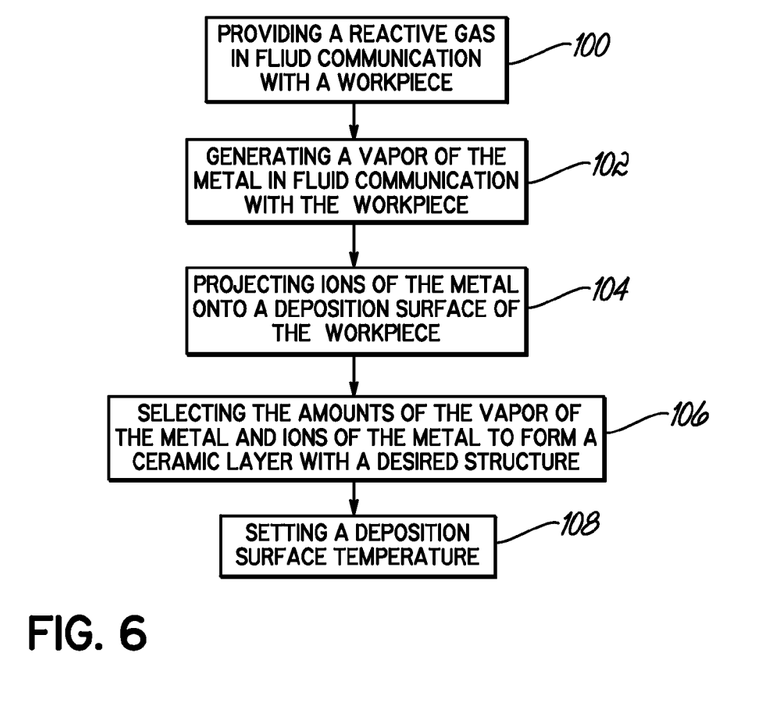
FIG. 6 is a diagram of another embodiment of the process of the present invention.

In another embodiment, the deposition surface 12, illustrated in FIG. 1B, of the workpiece 10 has a deposition surface temperature. With reference now to FIG. 6, the process includes controlling the deposition surface temperature in 108. The deposition surface temperature may influence the desired structure. While FIG. 6 illustrates a process wherein the deposition surface temperature is set following selecting the ratio of the metal vapor 32 to the metal ions 42, the process may alternate between setting the deposition surface temperature and selecting the ratio of the metal vapor 32 to the metal ions 42. Furthermore, setting the deposition surface temperature may occur many times during the process.

In one embodiment of the invention, the impingement of the ion beam may produce a deposition surface temperature greater than room temperature. The deposition surface temperature is less than approximately 1000° C. and may be limited by the workpiece's 10 material properties, such as its melting point. Thus, controlling the deposition surface temperature may require a heating system or a cooling system to attain or maintain the deposition surface temperature. The heating system may be an electrical resistance heating system as is known in the art. With reference to FIG. 1B, the cooling system may be, for example, cooling fluid passing through a work stage 60 supporting the workpiece 10, or the cooling fluid may impinge upon the deposition surface 12 or pass through the workpiece 10 itself. In another embodiment, the deposition surface temperature is greater than approximately 200° C. to substantially prevent water or other tenacious molecules from adhering to the deposition surface 12. In yet another embodiment, the deposition surface temperature is less than approximately 600° C. to avoid inadvertent heat treatment of the workpiece 10 or possible reaction of the workpiece 10 with the metal vapor 32, the metal ions 42, or the reactive gas 20.

In one embodiment of the invention, with reference to FIG. 1B, the metal vapor 32 is zirconium vapor, the metal ions 42 are zirconium ions, and the reactive gas 20 is oxygen. The ceramic layer 5 formed is zirconium dioxide, referred to herein as zirconia. The oxidizing gas 20 may have a pressure of less than approximately $2 \times 10^{-5}$ torr, or the partial pressure may be sufficient to oxidize substantially all of the zirconium ions 42 in the ion beam and the zirconium vapor 32 to form stoichiometric zirconia, i.e. $ZrO_2$. In any case, the pressure of the oxidizing gas 20 does not substantially interfere with impingement of the ion beam onto the deposition surface 12. A relationship between a ratio of an amount of the zirconium vapor 32 to an amount of the zirconium ions 42 which thereby forms a zirconia ceramic layer 5 is illustrated in FIG. 3 and tabulated in TABLE 1.

With reference to TABLE 1 and FIG. 1B, the "Ion Beam" column tabulates an ion beam voltage and an ion beam current supplied to the ion source 40 for projecting the ion beam of zirconium ions 42 onto the deposition surface 12. The "Evaporator" column lists an evaporator voltage and an evaporator current supplied to the evaporator 30 for generating the zirconium vapor 32. The "PE/PB" column is a calculated ratio of an evaporator power to an ion beam power. Furthermore, the evaporator power (PE) is a product of the evaporator current and the evaporator voltage. Similarly, the ion beam power (PB) is a product of the ion beam current and the ion beam voltage. The "% Monoclinic" column in TABLE 1 represents the volume fraction of the desired structure that is monoclinic zirconia. The % Monoclinic of the desired structure may be determined by x-ray diffraction, as discussed below.

Figure 3:
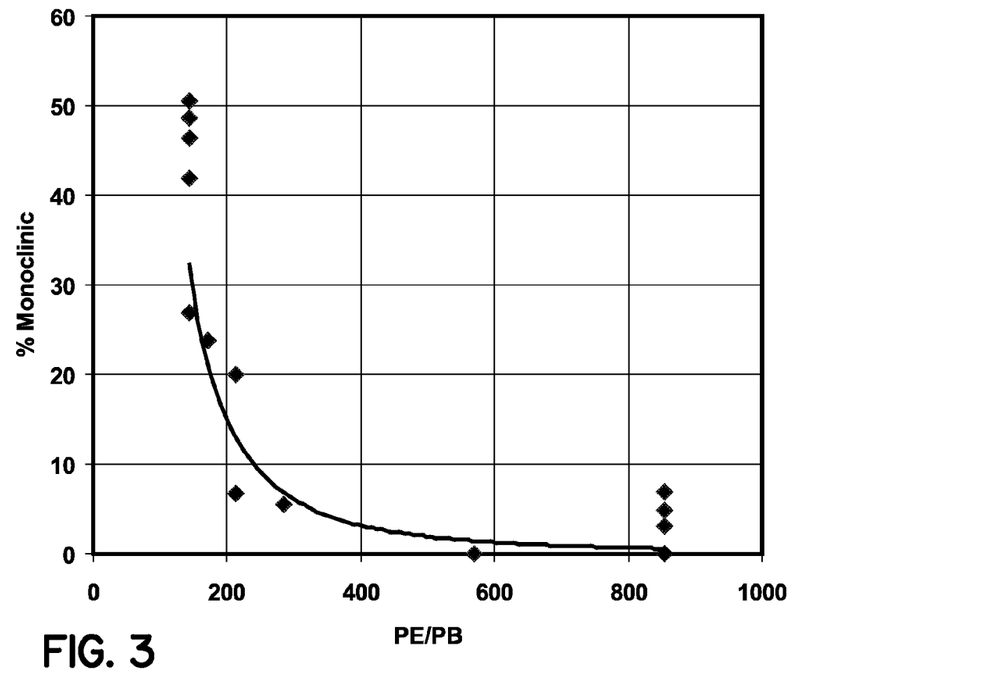
FIG. 3 illustrates a relationship between a ratio of a beam power and an evaporator power (PB/PE) and a desired structure having a predetermined ratio (% Monoclinic)

FIG. 3 is a plot of a portion of the data in TABLE 1. FIG. 3 illustrates a relationship between the ratio of the amount of the zirconium ions 42 to the amount of the zirconium vapor 32 and the desired structure of the zirconia ceramic layer 5. In one embodiment of the process, the evaporator power is related to the amount of the zirconium vapor 32 generated and projected onto the deposition surface 12, and the ion beam power is related to the amount of the zirconium ions 42 that impinge upon the deposition surface 12. As previously discussed, the PE/PB ratio is calculated from the ratio of the evaporator power and the ion beam power. Specifically, the PE/PB and % Monoclinic columns found in TABLE 1 are plotted as abscissa and ordinate in FIG. 3, respectively. Therefore, in general, as the evaporator power is increased relative to the ion beam power, the % Monoclinic in the desired structure approaches zero.

TABLE 1

| Ion Beam | | Evaporator | | | % |
|---|---|---|---|---|---|
| keV | μA | kV | mA | PE/PB | Monoclinic |
| 60 | 500 | 9.5 | 450 | 142.5 | 48.6 |
| 60 | 500 | 9.5 | 450 | 142.5 | 46.3 |
| 60 | 500 | 9.5 | 450 | 142.5 | 41.9 |
| 60 | 500 | 9.5 | 450 | 142.5 | 50.5 |
| 50 | 500 | 9.5 | 450 | 171.0 | 23.8 |
| 40 | 500 | 9.5 | 450 | 213.8 | 20.0 |
| 30 | 250 | 9.5 | 450 | 570.0 | 5.6 |
| 30 | 250 | 9.5 | 450 | 570.0 | 0 |
| 20 | 250 | 9.5 | 450 | 855.0 | 6.9 |
| 20 | 250 | 9.5 | 450 | 855.0 | 4.8 |
| 20 | 250 | 9.5 | 450 | 855.0 | 3.1 |
| 20 | 250 | 9.5 | 450 | 855.0 | 0 |

Therefore, selection of a particular PE/PB ratio will form a zirconia ceramic layer 5. The zirconia ceramic layer 5 may have at least two crystal phases formed in a predetermined ratio. In other words, the zirconia ceramic layer 5 comprises, a monoclinic phase formed according to a known % Monoclinic, as shown in FIG. 3.

In accordance with one embodiment of the present invention, with reference to FIG. 3, by selecting PE/PB ratios of between approximately 50 and approximately 1000, the zirconia ceramic layer 5 is formed with a desired structure comprising two crystal phases, including tetragonal and monoclinic zirconia. The predetermined ratio may be selected as greater than approximately 0 and less than approximately 60% Monoclinic, per FIG. 3.

In another embodiment, during selecting and adjusting, the ion beam power may be adjusted by changing the ion beam current and/or the ion beam voltage. For example, referring to TABLE 1, the ion beam power increases when the ion beam voltage is increased from 30 keV to 40 keV and the ion beam current is increased from 250 μA to 500 μA. Thus, by adjusting the ion beam power or the evaporator power, or both, the PE/PB ratio may be selected to be between approximately 50 and approximately 1000. In another embodiment of the process, the ion beam power is selected such that the PE/PB ratio is between approximately 100 and approximately 900. As one skilled in the art will observe, the PE/PB may depend upon the type of metal vapor 32 and the metal ions 42. Therefore, the evaporator power and ion beam power may vary significantly for other types of metal. In another embodiment of the instant invention, during the step of adjusting the ion beam power, the ion beam voltage is adjusted to between approximately 20 keV and approximately 60 keV, and the ion beam current is adjusted to between approximately 250 μA and approximately 500 μA.

Figure 2:
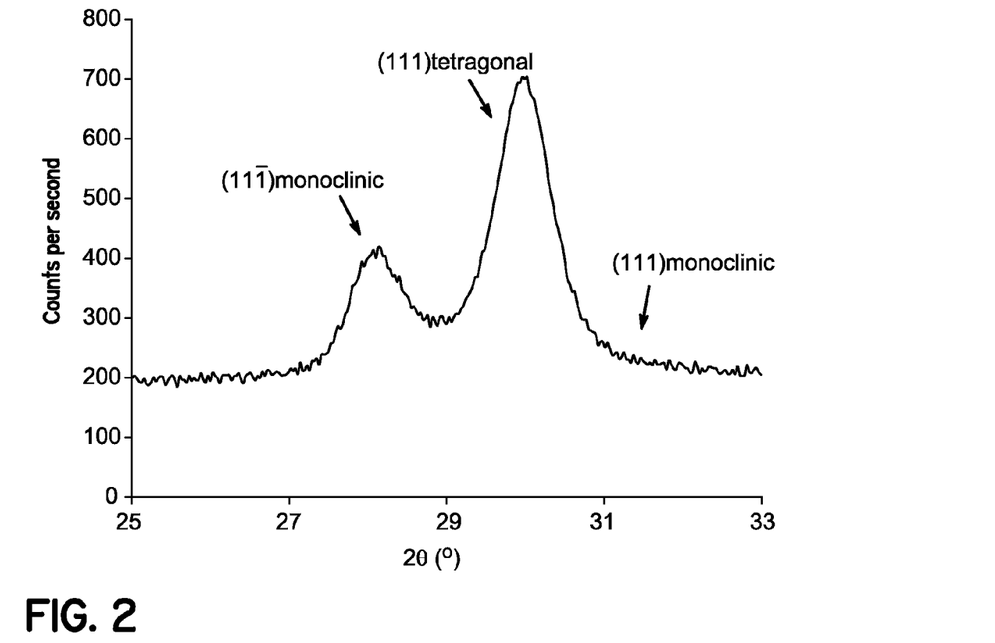
FIG. 2 is an illustration of an x-ray diffraction pattern taken of a ceramic layer comprising zirconia deposited according to one embodiment of the present invention.
Figure 5:
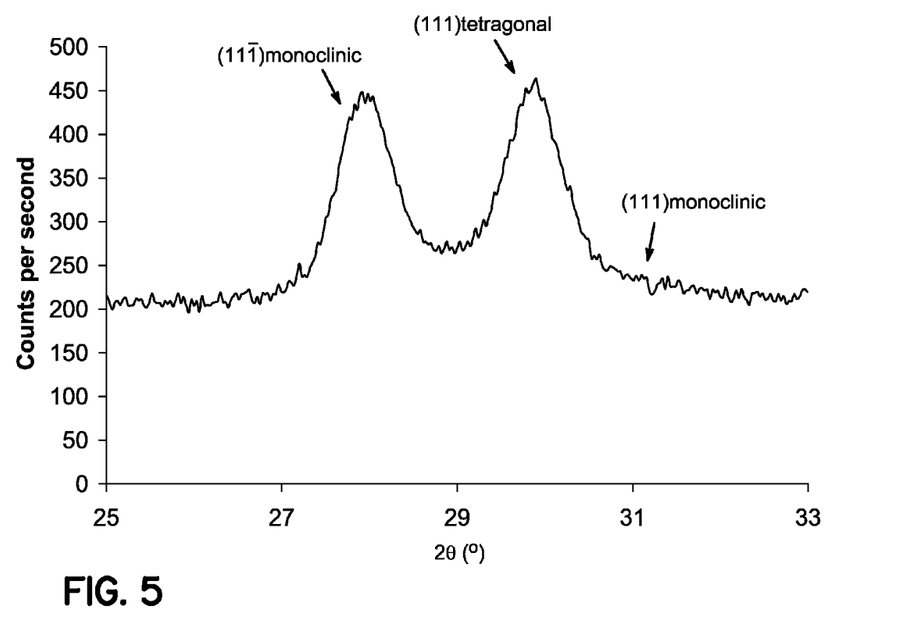
FIG. 5 is another illustration of an x-ray diffraction pattern of a zirconia ceramic layer deposited according to one embodiment of the present invention.

In another embodiment of the present invention, the monoclinic zirconia crystals may form with a preferred crystallographic orientation. FIGS. 2 and 5 are x-ray diffraction patterns of examples of the zirconia ceramic layer 5 formed according to one embodiment of the process. As shown in FIGS. 2 and 5, the (111) tetragonal and the (11$\bar{1}$) monoclinic peaks are present but the (111) monoclinic peak is absent from the x-ray diffraction pattern. As one skilled in the art will appreciate, the presence of the (11$\bar{1}$) monoclinic peak combined with the absence of the (111) monoclinic peak indicates a preferred orientation of the monoclinic crystals on the deposition surface. Therefore, during selecting or adjusting, the crystals may be formed with the preferred crystallographic orientation relative to the deposition surface 12.

Figure 7:
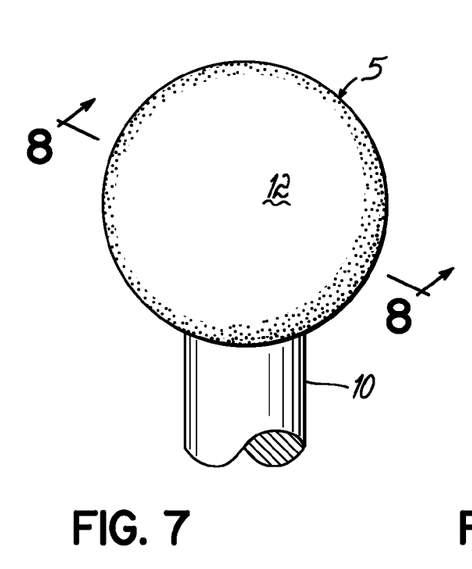
FIG. 7 is a perspective view of one embodiment wherein the workpiece is a femoral hip ball.
Figure 8:
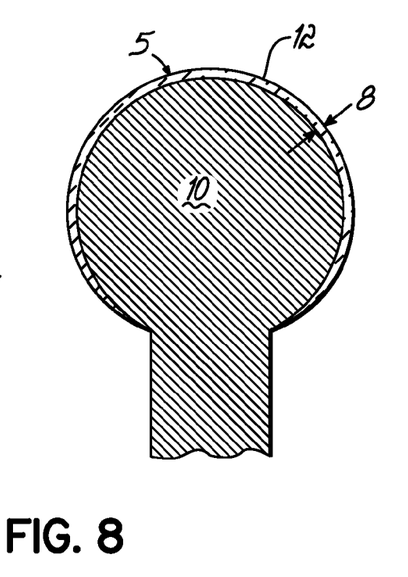
FIG. 8 is a cross-sectional view of the embodiment of FIG. 7, taken along section line 8-8.

In yet another embodiment, the predetermined ratio of monoclinic zirconia to tetragonal zirconia is selected to suppress the tetragonal to monoclinic phase transformation. As illustrated in FIGS. 1B, 7 and 8, the workpiece 10 is an orthopedic implant, and the process for forming the zirconia ceramic layer 5 is used to form the desired structure having a predetermined ratio of monoclinic zirconia to tetragonal zirconia on the deposition surface 12 of the orthopedic implant. By way of example and not limitation, the orthopedic implant may be a femoral hip ball implant or femoral knee implant, or other artificial joint. The zirconia ceramic layer 5 is formed as an articular surface on the orthopedic body. The predetermined ratio may be selected to suppress the tetragonal to monoclinic phase transformation such that the articular surface retains its smooth surface and does not roughen during use in vivo. In many of the embodiments, the zirconia ceramic layer 5 has a thickness 8 of less than approximately five microns for cost effective and efficient processing of orthopedic implants.

Figure 4:
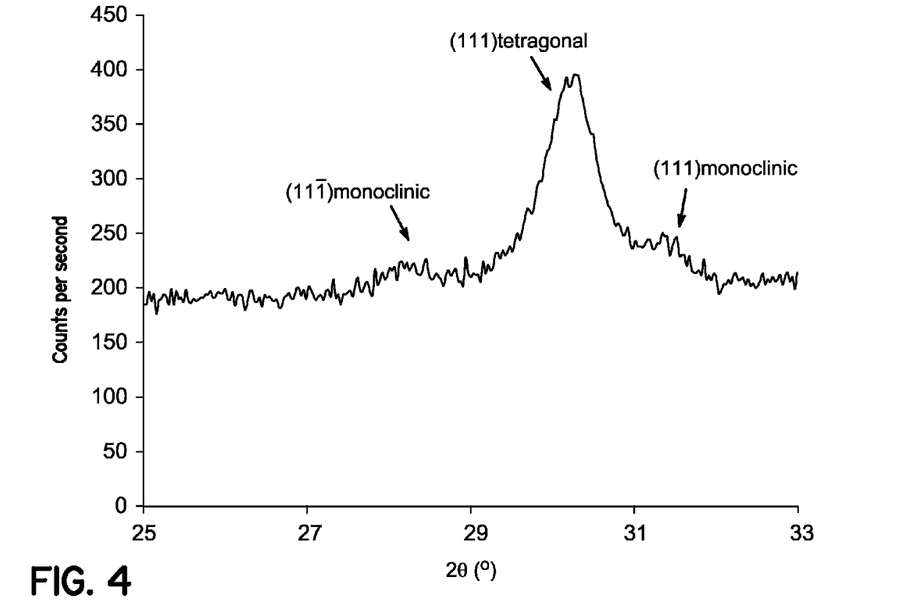
FIG. 4 is another illustration of an x-ray diffraction pattern of a zirconia ceramic layer deposited according to one embodiment of the present invention.

By way of example and not limitation, the desired structure was quantified with x-ray diffraction, as is known in the art. FIGS. 2, 4, and 5 are examples of x-ray diffraction data gathered from zirconia ceramic layers formed with one embodiment of the process of the present invention. A Scintag XDS 2000 x-ray diffractometer utilizing DMS 2000 software was used to gather the x-ray diffraction data. All scans were made in regular symmetric optics and a CuK-alpha radiation. An EG&G Ortec solid-state detector, model number GLP-10195/07-S was used to gather each x-ray diffraction pattern. Following phase identification, the relative volume of each crystal phase was determined by deconvoluting and peak fitting the x-ray diffraction patterns.

One method for quantifying the relative percentages of zirconia phases is with a method found in "Quantitative X-ray Diffraction Analysis of Polymorphic Mixes of Pure Zirconia," P. A. Evans, R. Stevens and J. G. P. Binner, Br. Ceram. Trans. J., vol. 83, pp. 39-43, 1984, incorporated by reference herein. As detailed in the article, the method uses the following equation to estimate the volume percent of each phase within the ceramic layer.

$$f_t = \frac{I_t(111)}{I_m(111) + I_m(11\bar{1}) + I_t(111)}$$

Where:
$f_t$ is a volume fraction of tetragonal zirconia
$I_t(111)$ is an integrated intensity of the tetragonal (111) peak
$I_m(111)$ is an integrated intensity of the monoclinic (111) peak
$I_m(11\bar{1})$ is an integrated intensity of the monoclinic (11$\bar{1}$) peak Ultimately, provided no cubic phase is detected, the fraction of monoclinic, $f_m$, is derived from $$f_m = 1 - f_t$$

To determine the various integrated intensities (e.g. $I_t(111)$, $I_m(111)$, $I_m(11\bar{1})$), background intensities were assumed to be linear over the narrow angular ranges used. The peaks were deconvoluted and fitted using a standard Pearson VII algorithm, as is known in the art.

As depicted in FIG. 2, in one exemplary x-ray diffraction pattern, the ceramic layer comprises both tetragonal and monoclinic zirconia. The ceramic layer has a (11$\bar{1}$) monoclinic diffraction peak and a (111) tetragonal diffraction peak indicating that the desired structure comprises two crystal phases of zirconia, i.e., a tetragonal zirconia and a monoclinic zirconia. Following peak fitting and deconvolution, the fraction of monoclinic, $f_m$, may be calculated. In turn, $f_m$ may be used to calculate a percent monoclinic. As depicted in FIG. 3, the "% Monoclinic" represents the ratio of the monoclinic zirconia to the tetragonal zirconia. As shown in TABLE 1, the % Monoclinic calculated from the x-ray diffraction pattern, shown in FIG. 2, is 20.0.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention is therefore not limited to the specific details, representative apparatus and process and illustrative examples shown and described. Accordingly, departures may be made from such details without departing from the scope of the general inventive concept.

What is claimed is:

1. A process for forming a ceramic layer comprising a compound of a metal on a deposition surface of an orthopedic implant, the process comprising:
   providing a reactive gas in fluid communication with the deposition surface of the orthopedic implant;
   generating a vapor of the metal in fluid communication with the deposition surface;
   projecting an ion beam comprising a plurality of ions of the metal onto the deposition surface; and
   selecting amounts of the vapor of the metal and the ions of the metal relative to each other, wherein the reactive gas, the vapor of the metal, and the ions of the metal react at the selected amounts to concurrently deposit two or more crystal phases of a ceramic material on the surface of the orthopedic implant to form a ceramic layer having the two or more crystal phases in a ratio that suppresses phase transformation between the monoclinic and tetragonal phases.

2. The process of claim 1 wherein the deposition surface has a deposition surface temperature, and the process further comprises controlling the deposition surface temperature to between approximately 25° C. and approximately 1000° C.

3. The process of claim 1 wherein the deposition surface has a deposition surface temperature, and the process further comprises controlling the deposition surface temperature to between approximately 200° C. and approximately 600° C.

4. The process of claim 1 wherein the reactive gas has a partial pressure sufficient to react with substantially all of the vapor of the metal and the ions of the metal.

5. The process of claim 1 wherein the reactive gas comprises oxygen having a partial pressure of less than approximately $2 \times 10^{-5}$ torr, the vapor of the metal comprises zirconium vapor, and the ions of the metal comprises zirconium ions, and wherein the oxygen, the zirconium vapor, and the zirconium ions react to form the ceramic layer, wherein the ceramic layer is a zirconia ceramic layer having two or more crystal phases at a predetermined ratio.

6. The process of claim 5 wherein the amounts of the zirconium vapor and the zirconium ions are selected relative to each other and the oxygen reacts with both the zirconium vapor and the zirconium ions to form the zirconia ceramic layer comprising two or more of a monoclinic phase, a tetragonal phase, or a cubic phase at the predetermined ratio on the deposition surface.

7. The process of claim 5 wherein the amounts of the zirconium vapor and the zirconium ions are selected relative to each other and the oxygen reacts with both the zirconium vapor and the zirconium ions to form the zirconia ceramic layer wherein one of the crystal phases comprises a monoclinic phase, and wherein the monoclinic phase has a plurality of monoclinic crystals with a preferred crystallographic orientation on the deposition surface.

8. The process of claim 5 wherein the amounts of the zirconium vapor and the zirconium ions are selected relative to each other and the oxygen reacts with both the zirconium vapor and the zirconium ions to form the zirconia ceramic layer wherein the crystal phases comprise a monoclinic phase and a tetragonal phase on the deposition surface.

9. The process of claim 8 wherein the monoclinic phase and the tetragonal phase form in a predetermined ratio of a volume of the monoclinic phase to a volume of the tetragonal phase and the predetermined ratio is between greater than 0 and approximately 0.6.

10. The process of claim 9 wherein the zirconium vapor is generated with an evaporator, an amount of the zirconium vapor is related to an evaporator power supplied to the evaporator, an amount of the zirconium ions in the ion beam is related to an ion beam power supplied to an ion source, and during selecting amounts of the zirconium vapor and the zirconium ions relative to each other, the ion beam power is selected such that a ratio of the evaporator power to the ion beam power is between approximately 50 and approximately 1000.

11. The process of claim 10 wherein the ion beam power is determined by an ion beam voltage and an ion beam current, and during selecting the amount of the zirconium ions, the ion beam voltage is selected between approximately 20 keV and approximately 60 keV and the ion beam current is selected between approximately 250 μA and approximately 500 μA.

* * * * *

UNITED STATES PATENT AND TRADEMARK OFFICE
CERTIFICATE OF CORRECTION

| | | |
|---|---|---|
| PATENT NO. | : 8,133,553 B2 | Page 1 of 1 |
| APPLICATION NO. | : 11/764585 | |
| DATED | : March 13, 2012 | |
| INVENTOR(S) | : Anderson et al. | |

It is certified that error appears in the above-identified patent and that said Letters Patent is hereby corrected as shown below:

Title page 2, Column 1, In the Citation of U.S. Patent Documents 5,383,934, Delete "Armini" and insert -- Armini et al. --, therefor.

Title page 2, Column 2, In the Citation of U.S. Patent Documents 6,540,746, Delete "Buehler" and insert -- Buehler et al. --, therefor.

Title page 3, Column 1, In the Citation of U.S. Patent Documents 2005/0015442 A1, Delete "Eidenschink" and insert -- Eric et al. --, therefor.

Title page 3, Column 2, In the Citation of U.S. Patent Documents 2006/0039947 A1, Delete "Schmidmaier" and insert -- Schmidmaier et al. --, therefor.

Signed and Sealed this
Eleventh Day of November, 2014

Michelle K. Lee
*Deputy Director of the United States Patent and Trademark Office*